US011022528B2

(12) United States Patent
Park et al.

(10) Patent No.: US 11,022,528 B2
(45) Date of Patent: Jun. 1, 2021

(54) COMPOSITION FOR BIOLOGICAL TISSUE TRANSPARENCY AND METHOD FOR BIOLOGICAL TISSUE TRANSPARENCY USING SAME (71) Applicant: KOREA RESEARCH INSTITUTE OF CHEMICAL TECHNOLOGY, Daejeon (KR)

(72) Inventors: Sun Hyun Park, Daejeon (KR); Ki-Suk Kim, Daejeon (KR); Dae-hwan Nam, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 23 days.

(21) Appl. No.: 16/604,113

(22) PCT Filed: Feb. 23, 2018

(86) PCT No.: PCT/KR2018/002240
§ 371 (c)(1),
(2) Date: Oct. 9, 2019

(87) PCT Pub. No.: WO2018/194253
PCT Pub. Date: Oct. 25, 2018

(65) Prior Publication Data
US 2020/0378876 A1 Dec. 3, 2020

(30) Foreign Application Priority Data

Apr. 21, 2017 (KR) .................. 10-2017-0051443
Aug. 21, 2017 (KR) .................. 10-2017-0105551

(51) Int. Cl.
*G01N 1/34* (2006.01)
*A61K 31/575* (2006.01)
*G01N 1/30* (2006.01)
*G01N 33/483* (2006.01)
*C07J 41/00* (2006.01)

(52) U.S. Cl.
CPC ............. *G01N 1/34* (2013.01); *A61K 31/575* (2013.01); *G01N 1/30* (2013.01); *G01N 33/4833* (2013.01);
(Continued)

(58) Field of Classification Search
CPC ........................................ G01N 1/34
See application file for complete search history.

(56) References Cited

U.S. PATENT DOCUMENTS 8,198,245 B2  6/2012  Niklason et al.
2014/0199686 A1  7/2014  Liu et al.
2017/0227430 A1  8/2017  Marini et al.

FOREIGN PATENT DOCUMENTS

JP   2003-066035 A   3/2003
JP   2010-168386 A   8/2010
(Continued)

OTHER PUBLICATIONS

Google Patents translation of Olympus Corp., JP 2015-049101 A, 2015.*
(Continued)

*Primary Examiner* — Rosanne Kosson
(74) *Attorney, Agent, or Firm* — Klarquist Sparkman, LLP (57) ABSTRACT

The clarity method for biotissue using a biotissue clearing agent including CHAPS of the present invention enables fast tissue clarity without denaturation.

7 Claims, 11 Drawing Sheets

(52) U.S. Cl.
CPC ..... *C07J 41/0033* (2013.01); *G01N 2001/305* (2013.01)

(56) References Cited

FOREIGN PATENT DOCUMENTS

| | | |
|---|---|---|
| JP | 2013-522590 A | 6/2013 |
| JP | 2015-049101 A | 3/2015 |
| KR | 2005-0118219 A | 12/2005 |
| WO | WO 2011/111876 A1 | 9/2011 |
| WO | WO 2014/069519 A1 | 5/2014 |
| WO | WO 2016/023009 A1 | 2/2016 |
| WO | WO 2016/108359 A1 | 7/2016 |
| WO | WO 2016/147812 A1 | 9/2016 |

OTHER PUBLICATIONS

Chung et al. "Structural and molecular interrogation of intact biological systems" *Nature* 497:332-338 (2013).

Calle et al. "The Use of Optical Clearing and Multiphoton Microscopy for Investigation of Three-Dimensional Tissue-Engineered Constructs" *Tissue Engineering* 20(7):570-577 (2014).

Lee et al. "Improved application of the electrophoretic tissue clearing technology, CLARITY, to intact solid organs including brain, pancreas, liver, kidney, lung, and intestine" *BMC Developmental Biology* 14(1):781 (2014) https://dash.harvard.edu/handle/1/13890801.

Susaki et al. "Whole-Brain Imaging with Single-Cell Resolution Using Chemical Cocktails and Computational Analysis" *Cell* 157:726-739 (2014).

Kagakutoseibutu "Figure 4 One-cell resolution three-dimensional anatomy / pathology at organ in individual scale" 53(11):737-740 (2015).

Richardson and Lichtman "Clarifying Tissue Clearing" *Cell* 162(2):246-257 (2015).

English-language translation of Written Opinion for PCT/KR2018/002240, dated May 23, 2018 (10 pages).

* cited by examiner

COMPOSITION FOR BIOLOGICAL TISSUE TRANSPARENCY AND METHOD FOR BIOLOGICAL TISSUE TRANSPARENCY USING SAME

CROSS REFERENCE TO RELATED APPLICATIONS

This is the U.S. National Stage of International Application No. PCT/KR2018/002,240, filed Feb. 23, 2018, which in turn claims the benefit of Korean Application No. 10-2017-0051443, filed Apr. 21, 2017 and Korean Application No. 10-2017-0105551, filed Aug. 21, 2017.

BACKGROUND OF THE INVENTION

1. Field of the Invention

The present invention relates to a clarity method for biotissue.

2. Description of the Related Art

The tissue clarity technique is useful for the confirmation of the internal structure and protein distribution of biotissue. In particular, this technique enables deeper observation of the tissue structure and the approach to the integrated structure and molecular information from various systems. So, techniques for clearing tissues with various ways are being developed.

The conventional method for clearing tissue is exemplified by Spatleholz, BABB, Scale S, and iDISCO, which are the methods for clearing tissues using an organic solvent, and ACT (active CLARITY technology), the polymer injection method. The methods above, except ACT, have a disadvantage of the reduced preservability of fluorescence and antigen. ACT has the antigen preservability of at least 90%, which is way higher than the method requiring binding a hydrogel polymer to a fixed protein such as CLARITY. However, the strong tissue fixation process in this method causes the loss of antigenicity and draws a limit in possible antibodies. Therefore, it is necessary to improve the technology.

In the recently developed tissue clarity technique based on 'CLARITY', a kind of a tissue network support that holds important substances for diagnosis such as DNA and protein is created by adding hydrogel to tissues and lipids are selectively removed (International Patent Publication No. WO 2016/108359).

However, to use the 'CLARITY' based technique above, the hydrogel support needs to be introduced into the tissue. At this time, if the concentration of the hydrogel is too high, the degree of coupling to protein is increased so that a tighter network structure is formed to make the tissue hard. When the tissue is hardened, the lipid becomes difficult to escape by a surfactant, indicating that the time required for clarity becomes longer. In addition, the method above has another problem of causing air and black particle deposition on the tissue surface or discoloring the tissue to yellow.

Besides, the 'CLARITY' based technique above is very complicated and requires a lot of additional equipments. For example, in order to clear brain alone, it costs over 30,000,000 Korean Won. This method can clear one at a time, meaning if it tries to clear the brain, it can only clear the brain alone, indicating the method is not economical and time-consuming. The bigger problem is that an antibody staining material is hard to pass through the polyacrylamide net structure.

Therefore, it is required to develop a novel technique to clear biotissue without damaging the structure and protein of the tissue in the course of inducing tissue clarity without using polyacrylamide.

SUMMARY OF THE INVENTION

It is an object of the present invention to provide a composition for clearing biotissue which enables fast tissue clarity without denaturation of the tissue.

It is another object of the present invention to provide a clarity method for biotissue which enables fast tissue clarity without denaturation.

It is also an object of the present invention to provide a clarity method for biotissue comprising the step of pretreating a saccharide solution.

It is further an object of the present invention to provide a kit for clearing biotissue facilitating the clarity of bi-tissue.

To achieve the above objects, the present invention provides a composition for clearing biotissue comprising the compound represented by formula 1 below, or the hydrate of the same.

[Formula 1]

In addition, the present invention provides a clarity method for biotissue comprising the step of clearing the fixed biotissue by contacting the fixed tissue with the composition of the invention.

The present invention also provides a clarity method for biotissue comprising the steps of pretreating the fixed biotissue with a saccharide solution; and clearing biotissue by contacting the pretreated tissue with the composition for clearing biotissue of the invention.

In addition, the present invention provides a kit for clearing biotissue comprising a pretreatment composition for clearing biotissue containing a saccharide solution; and a composition for clearing biotissue.

Advantageous Effect

The clarity method for biotissue using a biotissue clearing agent including CHAPS of the present invention not only enables fast tissue clarity without denaturation but also induces an excellent tissue clearing effect by taking advantage of the pretreatment with a saccharide solution before the clearing agent treatment.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Hereinafter, the present invention is described in detail.

In one aspect of the invention, the present invention provides a composition for clearing biotissue comprising the compound represented by formula 1 below, or the hydrate of the same.

[Formula 1]

Hereinafter, the composition for clearing biotissue of the invention is described in more detail.

The composition for clearing biotissue of the present invention removes the lipid component that blocks transmission of light and other molecules from the biotissue, does not cause structural degeneration of the protein, and serves to tighten the tissue.

In the composition for clearing biotissue of the invention, the concentration of the compound represented by formula 1 is preferably 2-55 w/v % (weight/volume %) and more preferably 4-50 w/v %. At this time, as the solution showing the concentration, simulated body fluid used in ordinary fields can be used, which is more precisely exemplified by distilled water, PBS (phosphate buffer saline), and TBS (tris buffer solution), but not always limited thereto.

If the concentration of the compound represented by formula 1 is less than 2 w/v %, the clarity speed of biotissue would be lowered significantly. If the concentration of the compound is higher than 55 w/v %, CHAPS represented by formula 1 would not be dissolved completely.

Further, the composition for clearing biotissue of the invention can additionally include a substance that can accelerate biotissue clearing by controlling osmotic pressure. At this time, the substance that can accelerate biotissue clearing is selected from the group consisting of urea, CHAPSO (3-([3-Cholamidopropyl]dimethylammonio)-2-hydroxy-1-propanesulfonate), sucrose, fructose, glycerol, diatrizoic acid, Triton X-100, Tween-20, 2,2'-thiodiethanol, isohexyl, chloral hydrate, and a combination thereof, but not always limited thereto.

The concentration of the substance that can accelerate biotissue clearing is preferably 5-80 w/v %, 5-75 w/v %, 10-70 w/v %, 5-50 w/v %, or 35-60 w/v %. If the concentration is less than 5 w/v %, the speed of biotissue clearing is too slow. If the concentration is higher than 80 w/v %, crystals would be formed or solubility would be very poor. In a preferred embodiment of the present invention, as the substance that can accelerate biotissue clearing, urea was used. At this time, the concentration of urea was 10-70 w/v % and more preferably 20-60 w/v %. The concentration of the substance that can accelerate biotissue clearing can be regulated properly along with the concentration of the compound represented by formula 1.

According to the conventional clarity method, a mounting solution has to be additionally purchased or prepared to adjust refractive index of the tissue and solution. However, the composition for clearing biotissue of the present invention does not require the solution to adjust refractive index, which saves production costs. Also, the conventional clarity method causes the tissue to swell, but the composition of the present invention does not cause any size changes of the tissue.

As explained hereinbefore, the composition for clearing biotissue of the invention does not require a high price electrophoresis apparatus and expensive solutions; can be applied to various biotissues such as brain, liver, lung, kidney, intestine, heart, muscle, and blood vessels, without damaging any of those tissues; does not cause bubble formation, color change, or dark sediment; and can improve clarity of biotissue, so that it can be effectively used as a composition for clearing biotissue.

The present invention also provides a clarity method for biotissue comprising the step of clearing the fixed biotissue by contacting the fixed tissue with the composition above.

Hereinafter, the clarity method for biotissue of the invention is described in more detail.

The clarity method for biotissue of the present invention contains the step of clearing the fixed biotissue by contacting the fixed tissue with the composition above.

Particularly, the clarity method for biotissue of the invention is characterized by making the light invade more deeply by making the biotissue clearer by changing the physiochemical characteristics of the biotissue by contacting the tissue with the compound represented by formula 1.

The clarity method for biotissue of the invention does not cause bubble formation, color change, and dark sediment, either, and instead improves clarity of biotissue without losing or distorting the information of the tissue by protein degeneration. In particular, it is helpful to use various fluorophores including GFP protein to obtain useful information of tissue.

In the clarity method for biotissue of the present invention, the biotissue is not limited as long as it does not lose antigenicity before clarification and can be fixed.

More particularly, the fixation of biotissue can be performed by the conventional method using paraformaldehyde, ethylene glycol diglycidyl ether, dipropylene glycol diglycidyl ether, 1,4-butanediol diglycidyl ether, glycerol polyglycidyl ether, glutaraldehyde, polyacrylamide, or a combination thereof, but not always limited thereto.

In a preferred embodiment of the present invention, treatment of CHAPS and urea mixture increased the structural cohesion of protein, did not cause denaturation, made the tissue harder, prevented tissue swelling in the process of tissue clearing, and prevented from cracking n the process of washing. As the solution showing the concentration, simulated body fluid used in ordinary fields can be used, which is more precisely exemplified by distilled water, PBS (phosphate buffer saline), and TBS (tris buffer solution), but not always limited thereto. The impregnation can be performed at 10° C.-50° C., 12-48° C., 14-46° C., 16-44° C., 18-42° C., 20-40° C., 24-39° C., 28° C.-38° C., 30° C.-37° C., or 33-34° C.

The clarity method for biotissue of the present invention can be applied to various vertebrate tissues, particularly to brain, blood vessel, liver, lung, kidney, pancreas, and intestine, and is useful for the clarification of whole biotissue at once.

Further, the present invention provides a method for detecting important information in the cleared tissue such as DNA, RNA, protein, and fluorescent signal, etc.

Protein or mRNA in the biotissue cleared by the method of the invention can be detected by GFP fluorescence or immunostaining. When the protein is fixed, during the fixing process, the amino groups are linked together to form a network, which gives stability. In the meantime, nucleic acid such as RNA or DNA does not have amino groups, indicating it is comparatively unstable in the fixed tissue. In particular, in the course of electrophoresis, the position thereof can be changed in the tissue due to the electric characteristics of the nucleic acid. On the other hand, the biotissue cleared by the method of the invention is excellent in fluorescence staining for GFP cells and Choline Acetyltransferase, the cholinergic neuron marker antibody.

The clarity method for biotissue of the present invention can give the image enabling the three-dimensional observation of the undamaged biotissue cell and molecule distribution. So, observation studies can be carried out with complete structure of several hundred micrometers more for various biotissues with complicated structures. Thus, this method can be effectively used to identify the causes of various diseases including brain disease by gathering necessary information from the tissue.

In another aspect of the invention, the present invention provides a clarity method for biotissue comprising the steps of pretreating the fixed biotissue with a saccharide solution; and clearing biotissue by contacting the pretreated tissue with the composition for clearing biotissue of the invention.

The saccharide above can be a monosaccharide, a disaccharide, and a polysaccharide, etc. Particularly, the monosaccharide herein can be fructose, galactose, glucose, or mannose; the disaccharide herein can be sucrose, lactose, maltose, trehalose, turanose, or cellobiose; and the polysaccharide herein can be dextran, diethylamino ethyl-dextran, dextrin, cellulose, or β-glucans. Preferably, sucrose can be used as the saccharide. The saccharide solution is preferably an aqueous solution containing a saccharide.

The saccharide concentration in the saccharide solution is preferably 10-70 w/v %, 20-60 w/v %, 25-50 w/v %, or 30-40 w/v %.

If the biotissue is treated with the saccharide solution above, the lipid components that prohibit the transmission of light and other molecules are removed from the biotissue in advance and the dehydration is induced. Consequently, the structural binding force between the reagent for immobilizing the tissue and the biotissue protein is increased, so that the denaturation can be prevented and the tissue can be made harder. In addition, the tissue can be prevented from being swollen during the clarity process and tissue-cracking in the course of the antibody treatment process and the washing process. However, if the saccharide concentration in the saccharide solution is less than 10 w/v %, such effects as mentioned above would not be induced. On the contrary, if the saccharide concentration in the saccharide solution is higher than 70 w/v %, the treatment is not economic.

The clarity method for biotissue above can be performed at 4° C.-50° C., 10-50° C., 12-48° C., 14-46° C., 16-44° C., 18-42° C., 20-40° C., 24° C.-39° C., 28° C.-38° C., 30° C.-37° C., or 33-34° C.

In another aspect of the invention, the present invention provides a kit for clearing biotissue comprising a pretreatment composition for clearing biotissue containing a saccharide solution; and a composition for clearing biotissue.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Experimental Example 1

Evaluation of Biotissue Clarity by CHAPS

To evaluate whether or not the biotissue clarity can be easily induced when the biotissue is contacted with the biotissue clearing agent containing CHAPS alone, the following experiment was performed. All the animal tests described in this statement were performed according to the guidance (Approval No. RS17003) of Committee for Animal Resources, Korea Institute of Toxicology.

Particularly, adult mice (8 weeks old) were anesthetized with isoflurane (1 cc/min), an inhalation anesthetic. To stain the mouse blood vessels, Lectin-488 (Cat #DL1174) was injected through the tail vein. 5 minutes after the injection, 50 mL of ice cold 1× PBS was perfused, and then ice cold PBS containing 4% PFA was perfused again. Organs were extracted and dipped in 4% paraformaldehyde and PFA solution, followed by incubation at 4° C. for 12 hours. At this time, the temperature for ice cold condition is not limited but preferably −20° C.-40° C.

Next, the sample (3 mm thick) was washed with 50 ml of PBS twice. The sample fixed by the process described above was incubated in 40% CHAPS aqueous solution (40% CHAPS in DW) at 37° C. at 120 rpm for 5 days. As for the control, the fixed sample was incubated in PBS at 37° C. at 120 rpm for 5 days. The results are shown in FIG. 1 and FIG. 2.

Figure 1:
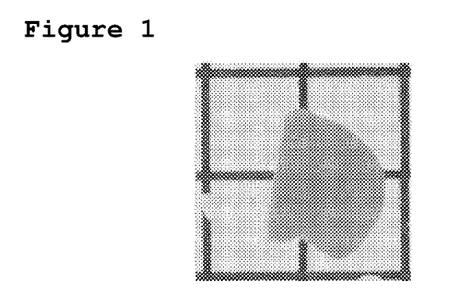
FIG. 1 is a photograph illustrating that the clarity of the mouse brain was not induced when the mouse was treated with PBS alone.

FIG. 1 is a photograph illustrating that the clarity of the mouse brain was not induced when the mouse was treated with PBS alone.

Figure 2:
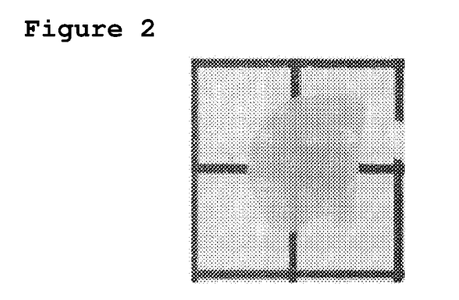
FIG. 2 is a photograph illustrating that the clarity of the mouse brain was induced when the mouse was treated with CHAPS alone.

FIG. 2 is a photograph illustrating that the clarity of the mouse brain was induced when the mouse was treated with CHAPS alone.

As shown in FIG. 1 and FIG. 2, when CHAPS was treated to the mouse brain alone, the clarity of the mouse brain was significantly induced. In addition, the treatment of CHAPS did not cause any changes in tissue size, from which it was confirmed that CHAPS could induce the biotissue clarity without causing denaturation or any damage of the tissue.

Experimental Example 2

Evaluation of Biotissue Clarity by CHAPS and Urea

To evaluate whether or not the biotissue clarity can be easily induced when the biotissue is contacted with the biotissue clearing agent containing CHAPS and urea, the following experiment was performed. All the animal tests described in this statement were performed according to the guidance (Approval No. RS17003) of Committee for Animal Resources, Korea Institute of Toxicology.

Particularly, adult mice (8 weeks old) were anesthetized with Isoflurane (1 cc/min), an inhalation anesthetic. To stain the mouse blood vessels, Lectin-488 (Cat #DL1174) was injected through the tail vein. 5 minutes after the injection, 50 mL of ice cold 1× PBS was perfused, and then ice cold PBS containing 4% PFA was perfused again. Organs were extracted and dipped in 4% paraformaldehyde and PFA solution, followed by incubation at 4° C. for 12 hours. At this time, the temperature for ice cold condition is not limited but preferably −20° C.-40° C.

Next, the sample was washed with 50 ml of PBS twice. The fixed sample was incubated in PBS containing CHAPS (20 w/v %) and urea (60 w/v %) at 37° C. at 220 rpm for 3 days. The results are shown in FIG. 1.

Figure 3:
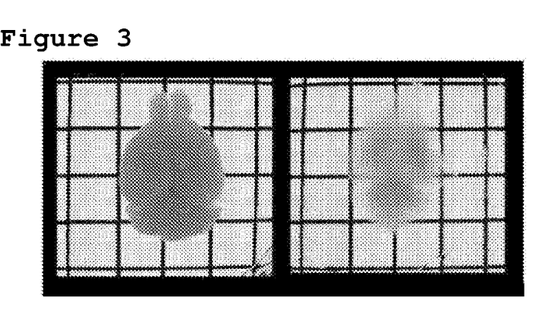
FIG. 3 is a set of photographs illustrating before and after the clarity of the mouse brain induced by the tissue clarity method of the present invention, wherein the left photograph shows the mouse brain before the clarity was induced and the right photograph shows the mouse brain after the clarity was induced.

FIG. 3 is a set of photographs illustrating before and after the clarity of the mouse brain induced by the tissue clarity method of the present invention, wherein the left photograph shows the mouse brain before the clarity was induced and the right photograph shows the mouse brain after the clarity was induced.

The mouse brain was transferred to tertiary distilled water from the PBS mixed solution comprising 20% CHAPS (w/v %) and 60% urea (w/v %), followed by washing the mouse brain with 50 ml of tertiary distilled water three times for 12 hours. The mouse brain was transferred to the mixed solution of CHAPS and urea (mounting solution), followed by observation of clarity of the mouse brain. The results are shown in FIG. 4.

Figure 4:
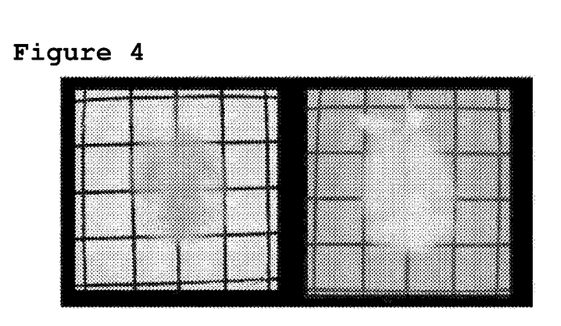
FIG. 4 is a set of photographs illustrating the mouse brain and the fluorescence intensity in the mouse brain completed with the clarity trough the tissue clarity method of the present invention, wherein the left photograph shows the mouse brain completed with the clarity process and the right photograph shows the intensity of GAD 67-GFP (Glutamic Acid Decarboxylase67-GFP) fluorescence in the mouse brain finished with the clarity process, observed by using ultraviolet (UV).

FIG. 4 is a set of photographs illustrating the mouse brain and the fluorescence intensity in the mouse brain completed with the clarity trough the tissue clarity method of the present invention, wherein the left photograph shows the mouse brain completed with the clarity process and the right photograph shows the intensity of GAD 67-GFP (Glutamic Acid Decarboxylase67-GFP) fluorescence in the mouse brain finished with the clarity process, observed by using ultraviolet (UV).

As shown in FIG. 3 and FIG. 4, it was confirmed that the biotissue clearing agent containing CHAPS and urea induced the biotissue clarity fast without causing denaturation of the tissue.

Experimental Example 3

Evaluation of Fluorescence Images of Biotissue Cleared by CHAPS and Urea

To investigate fluorescence in the brain cleared by the clarity method of the invention, the immunostained fluorescence and the green fluorescent protein (GFP) signals were confirmed in the mouse brain under the optical microscope (Leica) by using 1× objective lens. The results are shown in FIG. 5.

Figure 5:
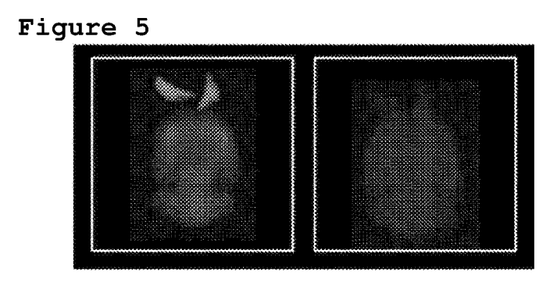
FIG. 5 is a set of photographs illustrating the fluorescence images of GAD67-GFP and Alexa fluor-647 in the mouse brain finished with the clarity process performed in Experimental Example 2, observed after treating the mouse with choline acetyltransferase antibody, wherein the left photograph shows the fluorescent image of GAD67-GFP and the right photograph shows the fluorescent image of Alexa fluor-647.

FIG. 5 is a set of photographs illustrating the fluorescence images of GAD67-GFP and Alexa fluor-647 in the mouse brain finished with the clarity process performed in Experimental Example 2, observed after treating the mouse with choline acetyltransferase antibody, wherein the left photograph shows the fluorescent image of GAD67-GFP and the right photograph shows the fluorescent image of Alexa fluor-647.

Figure 6:
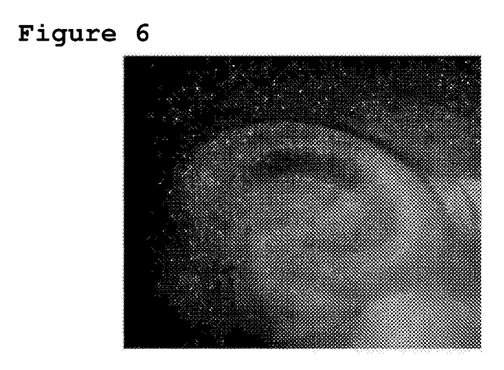
FIGS. 6, 7, and 8 are photographs illustrating the immuno-stained images and the GFP signals in the mouse brain finished with the clarity process in Experimental Example 2, observed under Microscopy Lightsheet Z.1 using 5× and 20× objective lens.
Figure 7:
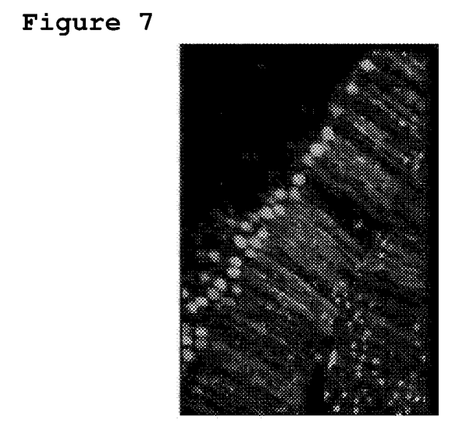
Figure 8:
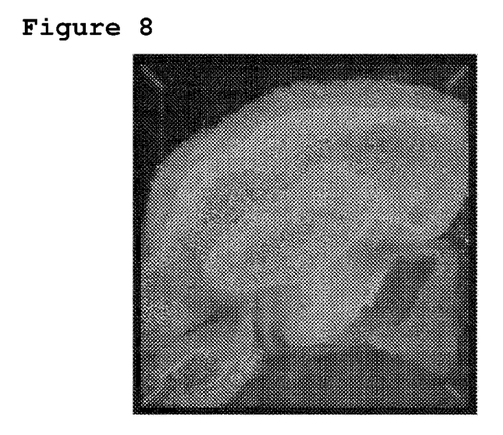

FIGS. 6, 7, and 8 are photographs illustrating the immunostained images and the GFP signals in the mouse brain finished with the clarity process in Experimental Example 2, observed under Microscopy Lightsheet Z.1 using 5× and 20× objective lens.

Figure 9:
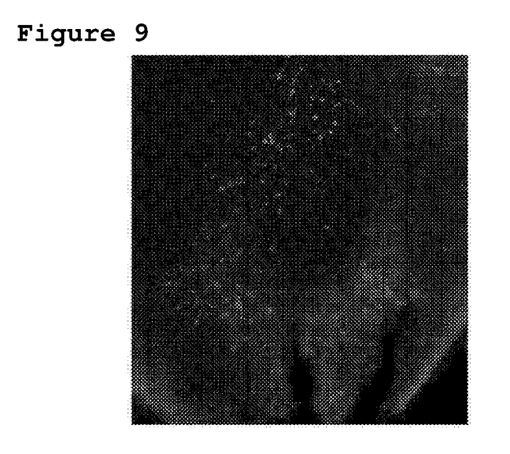
FIG. 9 is a photograph illustrating the combined fluorescence image of GAD67-GFP and Alexa fluor-647 in the mouse brain treated with tyrosine hydroxylase antibody, observed under Microscopy Lightsheet Z.1 using 5× objective lens.

FIG. 9 is a photograph illustrating the combined fluorescence image of GAD67-GFP and Alexa fluor-647 in the mouse brain treated with tyrosine hydroxylase antibody, observed under Microscopy Lightsheet Z.1 using 5× objective lens.

Figure 10:
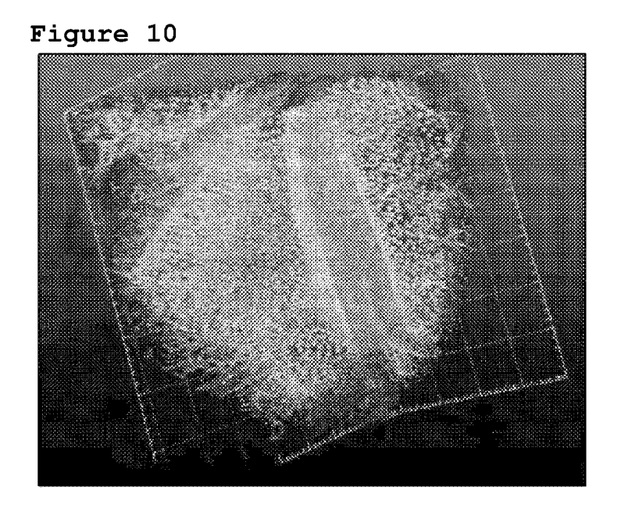
FIG. 10 is a photograph illustrating the combined fluorescence image of GAD67-GFP in the mouse brain finished with the clarity process in Experimental Example 2, observed after treating the mouse with Lectin-647 antibody.

FIG. 10 is a photograph illustrating the combined fluorescence image of GAD67-GFP in the mouse brain finished with the clarity process in Experimental Example 2, observed after treating the mouse with Lectin-647 antibody.

Figure 11:
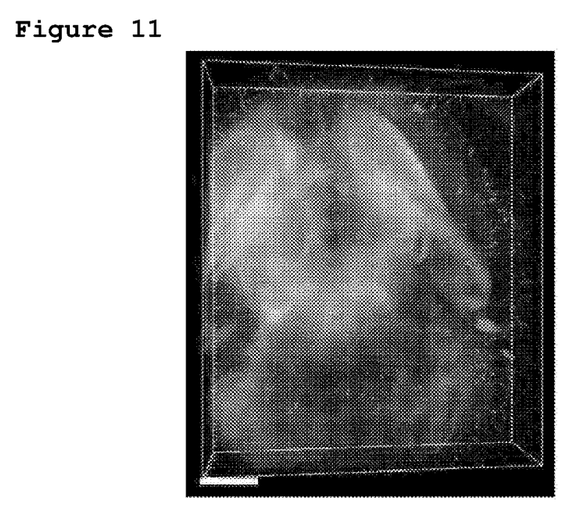
FIG. 11 is a photograph illustrating the fluorescent image obtained after treating the mouse brain finished with the clarity process in Experimental Example 2 with tyrosine hydroxylase antibody and staining the mouse brain with donkey anti-rabbit IgG Alexa fluor-647.

FIG. 11 is a photograph illustrating the fluorescent image obtained after treating the mouse brain finished with the clarity process in Experimental Example 2 with tyrosine hydroxylase antibody and staining the mouse brain with donkey anti-rabbit IgG Alexa fluor-647.

From the results above, it can be seen that the brain cleared by the clarity method of the present invention could be confirmed by fluorescence images.

Experimental Example 4

Evaluation of the Degree of Biotissue Clarity According to the Concentrations of CHAPS and Urea The following experiment was performed to investigate whether or not the biotissue clarity was affected by the changes of the concentrations of CHAPS and urea in the PBS mixed solution containing CHAPS and urea.

In Experimental Example 2, the PBS mixed solution comprising 20% CHAPS (w/v %) and 60% urea (w/v %) was used (20 C+60U %). In this example, clarity of the mouse brain was induced by the same manner as described in Experimental Example 2 except that the PBS mixed solution comprising 10% CHAPS (w/v %) and 65% urea (w/v %) (10 C+65U %) and the PBS mixed solution comprising 40% CHAPS (w/v %) and 45% urea (w/v %) (40 C+45U %) were used. The results are shown in FIG. 12.

Figure 12:
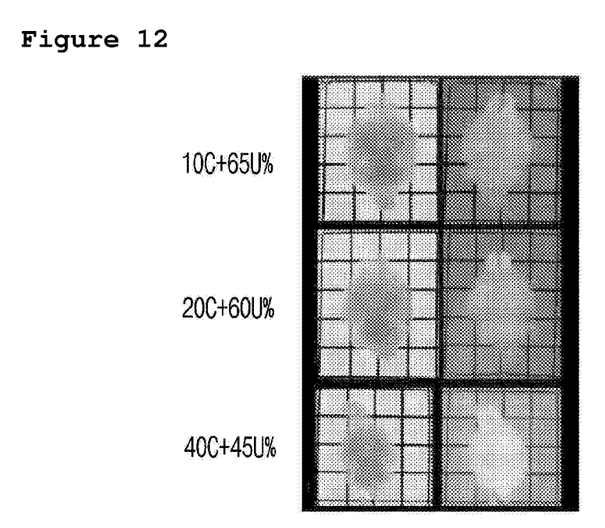
FIG. 12 is a set of photographs illustrating the changes of the degree of biotissue clarity according to the concentrations of CHAPS and urea in the PBS mixed solution comprising CHAPS and urea.

FIG. 12 is a set of photographs illustrating the changes of the degree of biotissue clarity according to the concentrations of CHAPS and urea in the PBS mixed solution comprising CHAPS and urea.

As shown in FIG. 12, the clarity of the mouse brain was induced without causing tissue denaturation in the PBS mixed solution comprising CHAPS and urea even when the concentration of CHAPS or urea was changed.

Experimental Example 5

Confirmation of the Superiority of the Composition Comprising CHAPS and Urea in Inducing Clarity When the clarity of biotissue was induced by the same manner as described in Experimental Example 2, sucrose or glycerol was used, instead of urea, together with CHAPS, leading to the preparation of the control group for the comparison of the biotissue clarity. The clarity of biotissue was also induced by using urea alone. In addition, the biotissue of the non-treated group treated with nothing was also observed. The results are shown in FIGS. 13-17.

Figure 13:
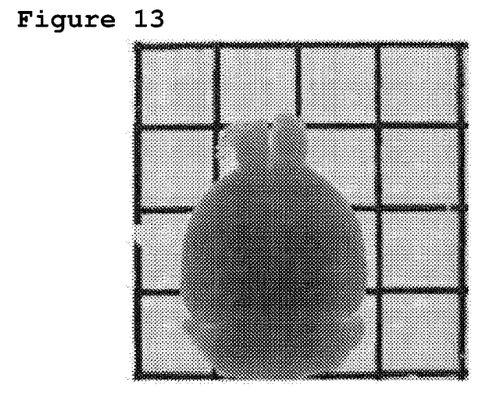
FIG. 13 is a photograph illustrating the image of the biotissue of the non-treated control group.

FIG. 13 is a photograph illustrating the image of the biotissue of the non-treated control group.

Figure 14:
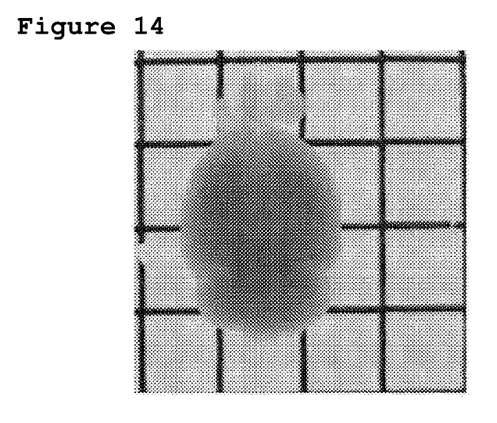
FIG. 14 is a photograph illustrating the result of inducing biotissue clarity by using 20 w/v % CHAPS and 50 w/v % sucrose.

FIG. 14 is a photograph illustrating the result of inducing biotissue clarity by using 20 w/v % CHAPS and 50 w/v % sucrose.

Figure 15:
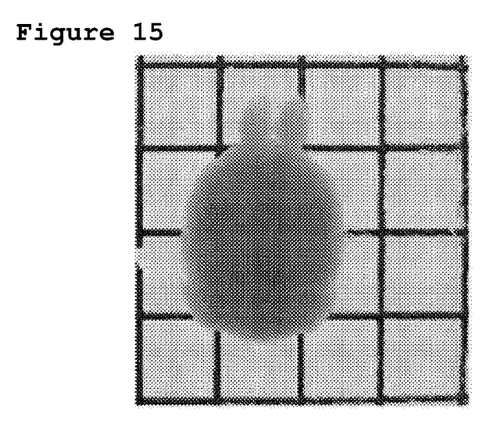
FIG. 15 is a photograph illustrating the result of inducing biotissue clarity by using 20 w/v % CHAPS and 75 w/v % glycerol.

FIG. 15 is a photograph illustrating the result of inducing biotissue clarity by using 20 w/v % CHAPS and 75 w/v % glycerol.

Figure 16:
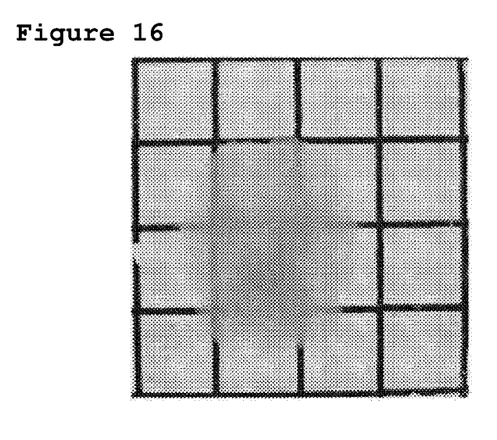
FIG. 16 is a photograph illustrating the result of inducing biotissue clarity by using 20 w/v % CHAPS and 50 w/v % urea.

FIG. 16 is a photograph illustrating the result of inducing biotissue clarity by using 20 w/v % CHAPS and 50 w/v % urea.

Figure 17:
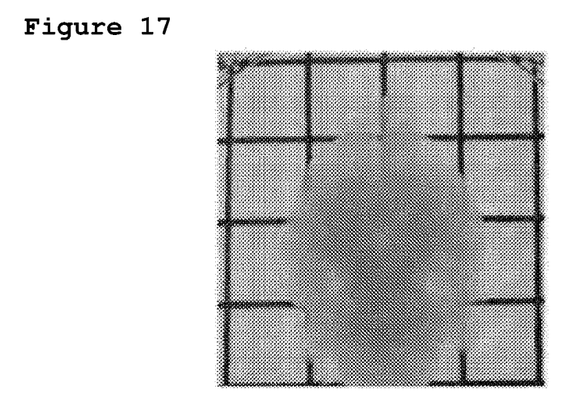
FIG. 17 is a photograph illustrating the result of inducing biotissue clarity by using PBS containing 60 w/v % urea.

FIG. 17 is a photograph illustrating the result of inducing biotissue clarity by using PBS containing 60 w/v % urea.

As shown in FIGS. 13-17, when the clarity of biotissue was induced with the biotissue clearing agent comprising CHAPS and urea, the clarity was fast induced without causing protein denaturation, compared with when the composition for clearing biotissue comprising sucrose or glycerol or the biotissue clearing agent containing urea alone was used.

In particular, the clarity of biotissue was induced with the biotissue clearing agent comprising CHAPS and urea, the clarity was completed within 5 days without causing any tissue denaturation (FIG. 16). When the clarity of biotissue was induced with the tissue clearing agent comprising urea alone, the brain tissue had a structural damage and the degree of clarity was reduced relatively even after 20 days (FIG. 17).

In the meantime, it was confirmed by the comparison between the case of treating CHAPS alone (FIG. 2) with the case of treating urea alone (FIG. 17) that the tissue was not only cleared but also had no size changes when CHAPS alone was treated, indicating that the brain tissue was not damaged, while the size of the tissue was increased by the treatment of urea alone, indicating that the brain tissue was damaged.

Experimental Example 6

Confirmation of Biotissue Clarity in the Condition of Preserved Tissue and Protein Structure from the Pretreatment of Saccharides The following experiment was performed to investigate if there would be any change in the degree of tissue clarity according to the pretreatment of saccharides. All the animal tests described in this statement were performed according to the guidance (Approval No. RS17003) of Committee for Animal Resources, Korea Institute of Toxicology.

Particularly, adult mice (8 weeks old) were anesthetized with Isoflurane (1 cc/min), an inhalation anesthetic. Then, 50 mL of ice cold 1× PBS was perfused, and ice cold 4% PFA (paraformaldehyde) was perfused again. Organs were extracted and dipped in 4% PFA (aqueous solution), followed by incubation at 4° C. for 24 hours. At this time, the temperature for ice cold condition is not limited but preferably 0° C.-10° C. (fixing step)

Next, the sample (organ) was incubated in 40% sucrose solution at 0° C.-10° C. for 24 hours. At this time, the sucrose concentration (40%) was presented by w/v % (weight/volume %), for which an aqueous solution was used. (pretreatment step)

For the control group, the fixing step was performed without performing the pretreatment step.

Figure 18:
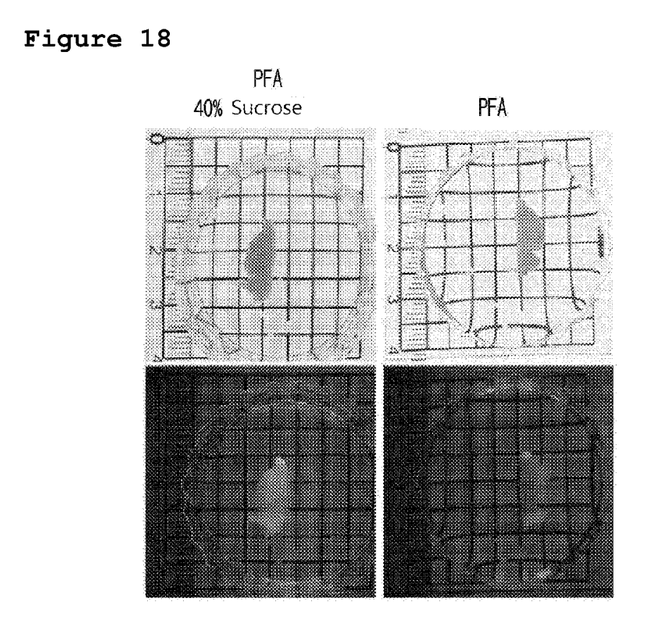
FIG. 18 is a set of photographs illustrating the results of the comparison of the mouse brain between the fixed mouse brain pre-treated with sucrose and the fixed mouse brain not treated with sucrose. The fluorescence images in the bottom part of FIG. 18 present the changes of the intensity of Glutamic Acid Decarboxylase67-GFP (GAD 67-GFP) fluorescence in the brain, measured by using ultraviolet (UV).

FIG. 18 is a set of photographs illustrating the image of the mouse brain finished with both the step of fixing and the step of pretreatment and the image of the mouse brain finished with the step of fixing only. The fluorescence images in the bottom part of FIG. 18 present the changes of the intensity of Glutamic Acid Decarboxylase67-GFP (GAD 67-GFP) fluorescence in the brain, measured by using ultraviolet (UV).

The sample tissues were incubated in the mixed solution comprising 20 w/v % CHAPS, 50 w/v % urea, and 50 mM sodium azide at 35° C. at 100 rpm for 5 hours or for 48 hours. (clearing step)

At this time, the said CHAPS indicates the compound represented by formula 1 of the invention or its hydrate.

Figure 19:
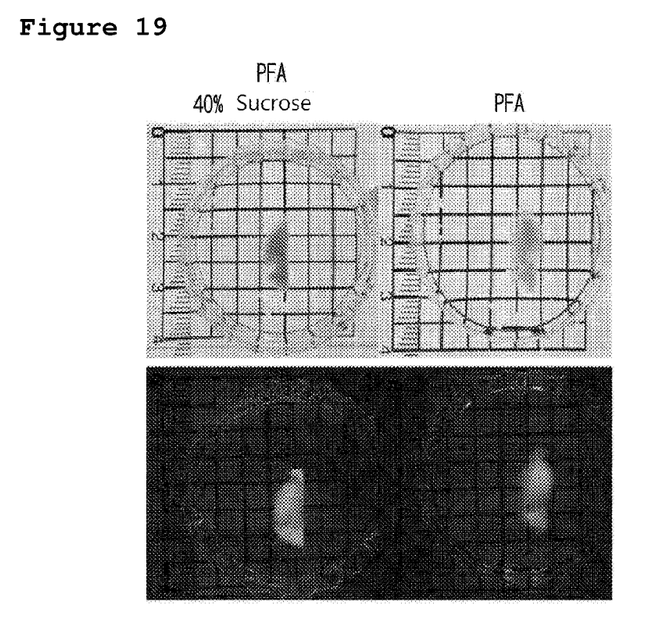
FIG. 19 is a set of photographs illustrating the results of the comparison of the mouse brain between the fixed mouse brain pre-treated with sucrose and finished with the clarity process by using a clearing agent for 5 hours and the fixed mouse brain finished with the clarity process by using a clearing agent for 5 hours. The fluorescence images in the bottom part of FIG. 19 present the changes of the intensity of Glutamic Acid Decarboxylase67-GFP (GAD 67-GFP) fluorescence in the brain, measured by using ultraviolet (UV).

FIG. 19 is a set of photographs illustrating the image of the mouse brain finished with all the steps of fixing, pretreatment, and clearing for 5 hours and the image of the control group mouse brain finished with the steps of fixing and clearing without the pretreatment step. The fluorescence images in the bottom part of FIG. 19 present the changes of the intensity of Glutamic Acid Decarboxylase67-GFP (GAD 67-GFP) fluorescence in the brain, measured by using ultraviolet (UV).

Figure 20:
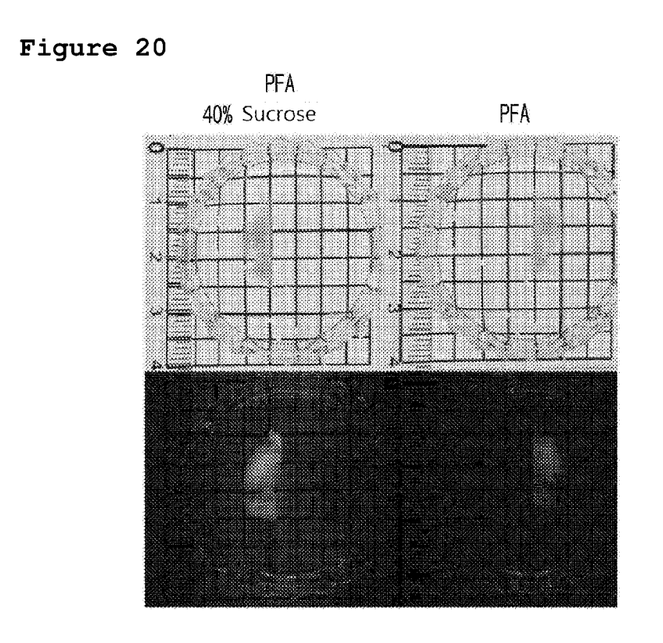
FIG. 20 is a set of photographs illustrating the results of the comparison of the mouse brain between the fixed mouse brain pre-treated with sucrose and finished with the clarity process by using a clearing agent for 48 hours and the fixed mouse brain finished with the clarity process by using a clearing agent for 48 hours. The fluorescence images in the bottom part of FIG. 20 present the changes of the intensity of Glutamic Acid Decarboxylase67-GFP (GAD 67-GFP) fluorescence in the brain, measured by using ultraviolet (UV).

FIG. 20 is a set of photographs illustrating the image of the mouse brain finished with all the steps of fixing, pretreatment, and clearing for 48 hours and the image of the control group mouse brain finished with the steps of fixing and clearing without the pretreatment step. The fluorescence images in the bottom part of FIG. 20 present the changes of the intensity of Glutamic Acid Decarboxylase67-GFP (GAD 67-GFP) fluorescence in the brain, measured by using ultraviolet (UV).

As shown in FIG. 19 and FIG. 20, the intensity of fluorescence was maintained in the mouse brain pretreated with sucrose when the tissue clarity was induced with CHAPS and urea, compared with the mouse brain non-pretreated with sucrose. In the meantime, the intensity of GFP fluorescence was reduced in the mouse brain non-pretreated with sucrose. The decrease of GFP fluorescence indicates that the protein structure was damaged. Therefore, it was confirmed that the pretreatment of sucrose was an important step to maintain the protein structure.

Accordingly, it was confirmed that the clarity method for biotissue containing the step of saccharide pretreatment of the present invention is significantly efficient in maintaining the protein structure, compared with the clarity method for biotissue not containing the step of saccharide pretreatment.

Experimental Example 7

Confirmation of Biotissue Clarity After Washing Process

The following experiment was performed to investigate the changes of the degree of tissue clarity according to the presence or absence of the saccharide pretreatment when the tissue cleared in Experimental Example 6 was washed and cleared again.

Figure 21:
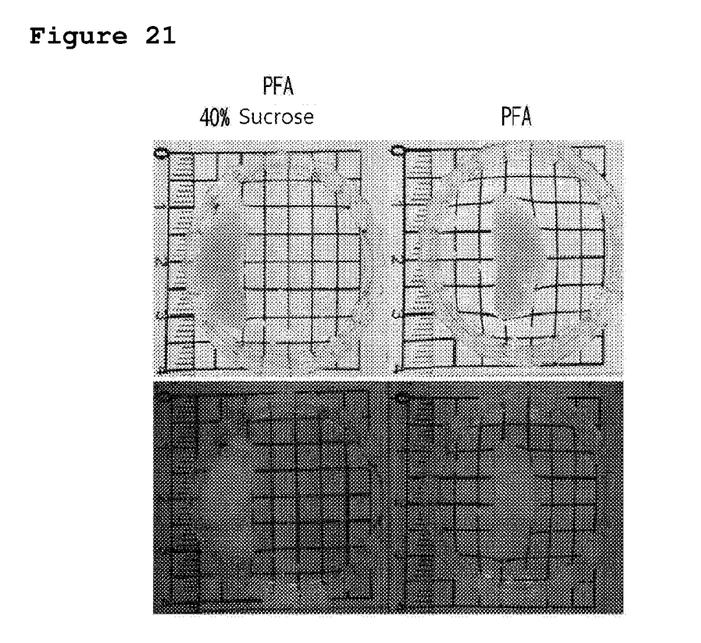
FIG. 21 is a set of photographs illustrating the images of the mouse brain processed with clarity, observed after the incubation of the brain in sterile distilled water. The fluorescence images in the bottom part of FIG. 21 present the changes of the intensity of Glutamic Acid Decarboxylase67-GFP (GAD 67-GFP) fluorescence in the brain, measured by using ultraviolet (UV).

The tissue cleared in Experimental Example 5 was incubated in 50 ml of sterile distilled water at 0° C.-10° C. at 20 rpm for 24 hours, during which the sterile distilled water was replaced three times (FIG. 21).

Figure 22:
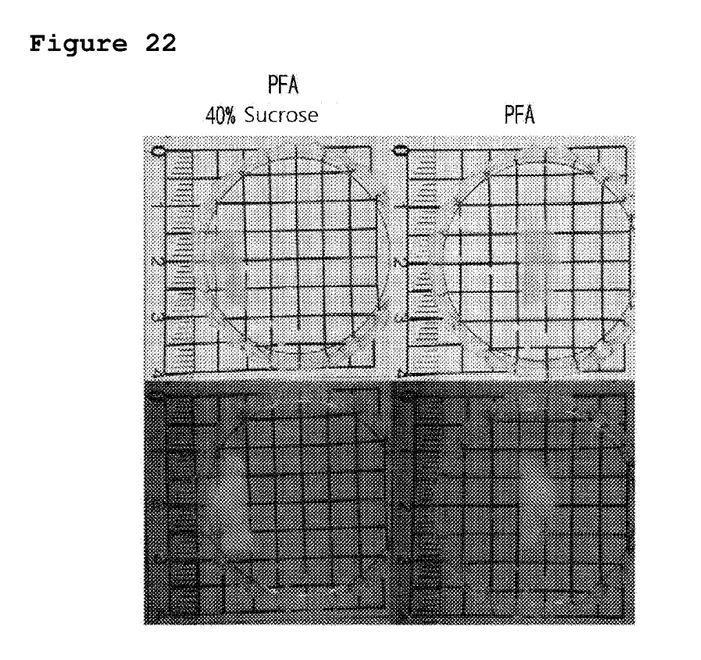
FIG. 22 is a set of photographs illustrating the results of the clarity induced in the mouse brain by using a clearing agent after washing the brain with sterile distilled water. The fluorescence images in the bottom part of FIG. 22 present the changes of the intensity of Glutamic Acid Decarboxylase67-GFP (GAD 67-GFP) fluorescence in the brain, measured by using ultraviolet (UV).

Then, the tissue was further incubated in the mixed aqueous solution comprising 20 w/v % CHAPS, 50 w/v % urea, and 50 mM sodium azide at 35° C. at 100 rpm for 24 hours (FIG. 22).

As shown in FIG. 22, the clarity of the tissue was significantly improved when the tissue was loaded again in the clearing solution after washing the tissue. Therefore, the washing process was also very important for the tissue clarity. Further, the fluorescence intensity in the mouse brain pretreated with sucrose was maintained even after performing washing and clearing thereof. On the other hand, the intensity of GFP fluorescence in the mouse brain which was not pretreated with sucrose was reduced. The decrease of GFP fluorescence indicates that the protein structure was damaged. Therefore, it was confirmed that the pretreatment of sucrose was an important step to maintain the protein structure.

From the results above, it was confirmed that the pretreatment with 40% sucrose according to the present invention was significantly efficient in protecting protein and tissue from being damaged by the composition for clearing biotissue and in maintaining fluorescence in the cleared tissue.

INDUSTRIAL APPLICABILITY

The clarity method for biotissue using a biotissue clearing agent containing CHAPS is useful for clearing biotissue.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A clarity method for clearing fixed biotissue, comprising the steps of:
    a) pretreating the fixed biotissue with a solution comprising an effective amount of a saccharide; and
    b) clearing the pretreated biotissue by contacting the pretreated biotissue with a composition comprising an effective amount of the compound represented by formula 1 below, or the hydrate of the same:

[Formula 1]

-continued

2. The clarity method for biotissue according to claim 1, wherein the saccharide is one or more materials selected from the group consisting of monosaccharides, disaccharides, and polysaccharides.

3. The clarity method for biotissue according to claim 2, wherein the monosaccharide is fructose, galactose, glucose, or mannose; the disaccharide is sucrose, lactose, maltose, trehalose, turanose, or cellobiose; and the polysaccharide is dextran, diethylamino ethyl-dextran, dextrin, cellulose, or β-glucans.

4. The clarity method for biotissue according to claim 1, wherein the saccharide solution is an aqueous solution containing a saccharide.

5. The clarity method for biotissue according to claim 1, wherein the saccharide concentration in the saccharide solution is 10-70 w/v %.

6. The clarity method for biotissue according to claim 2, wherein saccharide is a disaccharide.

7. The clarity method for biotissue according to claim 6, wherein the disaccharide is sucrose.

* * * * *